(12) United States Patent
Germiquet et al.

(10) Patent No.: US 6,885,201 B2
(45) Date of Patent: Apr. 26, 2005

(54) PORTABLE ELECTRONIC DEVICE INCLUDING CAPACITIVE WATER DETECTION MEANS AND METHOD OF IMPLEMENTATION

(75) Inventors: Christophe Germiquet, Prêles (CH); Vincent Berseth, Neuchâtel (CH); Jean-Jacques Born, Morges (CH)

(73) Assignee: Asuiab S.A. (CH)

( * ) Notice: Subject to any disclaimer, the term of this patent is extended or adjusted under 35 U.S.C. 154(b) by 0 days.

(21) Appl. No.: 10/706,960

(22) Filed: Nov. 14, 2003

(65) Prior Publication Data
US 2004/0108861 A1 Jun. 10, 2004

(30) Foreign Application Priority Data
Dec. 5, 2002 (CH) ................................. 2064/02

(51) Int. Cl.⁷ ............................................... G01R 27/26
(52) U.S. Cl. ........................ 324/663; 324/688; 324/690; 73/73
(58) Field of Search ................. 324/658–690; 73/73

(56) References Cited

U.S. PATENT DOCUMENTS 4,909,070 A * 3/1990 Smith ............................ 73/73

FOREIGN PATENT DOCUMENTS

| EP | 689 109 A1 | 12/1995 |
|---|---|---|
| EP | 745 915 A2 | 12/1996 |
| JP | 60 183896 U | 12/1985 |

* cited by examiner

Primary Examiner—Vincent Q. Nguyen
(74) Attorney, Agent, or Firm—Sughrue Mion, PLLC

(57) ABSTRACT

There is described a portable device (1) including in particular a case (2) closed by a glass (3) and containing device for detecting the presence of water (22) in contact with an external region of the assembly formed by the case and the glass. In a preferred embodiment, the device for detecting the presence of water include a plurality of capacitive sensors (20) arranged in a peripheral region of the device (1) so as to undergo a variation in their respective capacitances when the latter is immersed in water. Thus, a quantity characteristic of the capacitance value of each sensor (20) is periodically measured and stored. After each measurement, the new value obtained is compared to the preceding one to detect any variation in the corresponding capacitance. When a part of the capacitive sensors (20) simultaneously see their respective capacitances vary considerably between two measurements, detection of the presence of water is validated.

20 Claims, 2 Drawing Sheets

PORTABLE ELECTRONIC DEVICE INCLUDING CAPACITIVE WATER DETECTION MEANS AND METHOD OF IMPLEMENTATION

FIELD OF THE INVENTION

The present invention concerns a portable electronic device including powering means for powering electronic circuits including in particular, a data processing unit, the electronic circuits being housed in an assembly formed of a case closed by a glass, the device further including a pressure sensor and means for detecting the presence of water capable of producing electric signals to be sent to the data processing unit, the detection means including at least one capacitive sensor including, in particular, a capacitor one plate of which is formed by an electrode arranged on an inner region of the case-glass assembly, the capacitance of this capacitor being capable of varying following a modification in the nature of the external medium located directly in contact with an external region of the case-glass assembly facing said electrode, such as said external region coming into contact with water.

The present invention also concerns a method for implementing the means for detecting the presence of water in this type of device.

BACKGROUND OF THE INVENTION

Electronic devices of this type have already been described in the state of the art.

Japanese Utility Model No. 60-183896, published on 6 Dec. 1985, discloses an electronic apparatus fitted with means for measuring and displaying a depth of immersion in water, including, in particular, a pressure sensor. Because of the high electric energy consumption linked to operation of the pressure sensor, means for detecting the presence of water were provided on the apparatus to control the power supply to the pressure sensor, in order to interrupt said supply when the person wearing the apparatus is not in water. Thus, the solution proposed consists in using a capacitive sensor including a transparent electrode arranged on the inner face of the glass. This capacitive sensor causes a capacitance to appear when water is in contact with the glass, which causes modification of a reference signal passing through electronic processing circuits. Thus, the pressure sensor is only supplied with energy when water has been detected in contact with the glass of the apparatus.

It should be noted first of all that numerous devices are known wherein ohmic type means for detecting the presence of water are implemented. These detection means, although having generally reasonable electric power consumption, have a significant drawback, in that they require more or less complex construction. In particular, an aperture has to be provided in the case of the device, which can raise problems of water resistance. For this reason in particular, the Applicant has preferred to concern himself with improving capacitive type detection systems, which remove the need to make a specific aperture in the case of the device.

The technical solution presented in the aforecited Japanese Utility Model has, however, a certain number of drawbacks. In particular, a main switch is provided for controlling the power supply to the pressure sensor, operating in conjunction with the means for detecting the presence of water. In a certain way the water presence detection means fulfil the role of a secondary switch. The direct consequence of the presence of the main switch is that it is impossible to carry out pressure measurements when the apparatus is not immersed in water, which can be useful in certain cases as will be explained hereinafter. Moreover, the location kept for arranging the main switch is such that the water presence detection means are permanently powered from a clock signal. These detection means are thus responsible for a long-term waste of energy insofar as a test for the presence of water is permanently occurring and, in that the function of the secondary switch of the means for cutting the power supply to the pressure sensor is downstream of the detection means.

It should also be noted that the solution proposed does not take account of the fact that the structure described for the capacitive sensor has a stray capacitance, which imposes selection of a relatively high value for the capacitance formed at the glass of the apparatus, to allow the detection means to operate efficiently. Consequently, an additional drawback thus arises from the fact that the electric power consumption of the detection means is high because of the high value of the capacitance. The value chosen for the capacitance has to be even higher given that the stray capacitance is capable of varying as a function of the environmental conditions to which the apparatus is subjected, particularly as a function of temperature. Likewise, since detection of the presence of water occurs by detecting modifications of the reference signal, and since the amplitude of these modifications varies with the value of the capacitance that appears because of the presence of water, said capacitance has to have a value sufficient to make the amplitude of the modifications detectable by the electronic processing circuits.

Moreover, the value of the stray capacitance is capable of fluctuating over the long term, which can give rise to a malfunction of the detection means, in particular because the measurements carried out are absolute and not comparative.

SUMMARY OF THE INVENTION

It is a first object of the present invention to overcome the aforementioned drawbacks of the prior art by providing an apparatus including capacitive type means for detecting the presence of water and having low electric power consumption, and increased long term reliability within a broad range of environmental conditions.

The invention therefore provides a portable electronic apparatus of the type indicated hereinbefore, characterized in that the pressure sensor operates in at least two powering modes, a first so called surface mode and a second so-called dive mode, and in that the detection means are activated periodically to carry out measurements of a quantity representative of the capacitor capacitance, the detection means further including means for comparing at least two successive measurements of said quantity and-for producing an electric signal for activating the dive powering mode in response to a variation between two successive measurements of the quantity higher than a predefined value.

In a preferred embodiment, there is provided a plurality of capacitive sensors regularly distributed over the glass of the device, a quantity representative of the capacitance of each of these sensors being measured at each powering period of the detection means, in order to limit the inadvertent triggering of the dive powering mode capable of occurring with a single sensor. The detection means are thus arranged so as to activate the dive powering mode when a part of the measured quantities, preferably at least half or even all of them, vary more than the predefined value. Such a structure in fact enables a larger portion of the total surface area of the glass to be analysed to prevent, for example, the pressure sensor powering being activated as soon as the person wearing the device puts a finger on the glass.

Alternatively, a single electrode could be arranged on the inner face of the glass, this electrode substantially covering the whole of the surface of the glass. A trigger threshold could then be provided, corresponding to a predefined value for the proportion of the glass that is covered, insofar as the capacitance of the capacitive capacitor is a function of the covered surface. By way of example, it could be arbitrarily decided that, when the value of the measured quantity corresponds to the case in which half of the total surface of the glass is covered, it is assumed that the device is immersed. Consequently, with respect to the operation of the main embodiment described hereinbefore, the variation in the measured quantity between two successive measurements has to exceed a new predefined value having a higher value than that of the aforementioned predefined threshold, in order to activate the dive powering mode.

Preferably, the means for detecting the presence of water according to the present invention are implemented in a diving computer type device, or wristwatch type incorporating diving dedicated functions. In this latter case, it is desirable for the pressure measurements to be carried out regularly even when the user is not in a diving situation. Such measurements can be taken into account in the algorithm calculations implemented in the watch, to improve accuracy in determining the parameters of a dive.

Moreover, an additional use of the capacitive sensors can be envisaged when the device is not immersed such that they also fulfil a manual control member function.

The present invention also concerns a method for implementing means for detecting the presence of water like those described hereinbefore.

BRIEF DESCRIPTION OF THE DRAWINGS

The invention will be better understood using the following description of different embodiments with reference to the annexed drawings, in which.

DETAILED DESCRIPTION OF THE PREFERRED EMBODIMENTS

Figure 1:
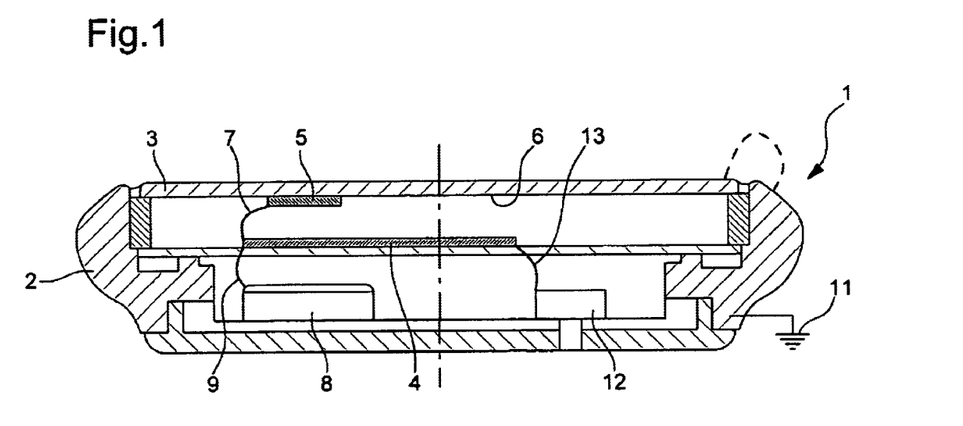
FIG. 1 is a schematic transverse cross-section of a preferred embodiment of the device according to the present invention.

FIG. 1 shows a cross-section of an electronic device 1 schematically represented in a non-limiting manner in the form of a wristwatch type device, including a case 2 and a glass 3. Electronic circuits 4 are arranged inside case 2. In accordance with a structure known in the prior art, a conductive electrode 5, preferably transparent, is arranged on inner face 6 of glass 3 of device 1. A conductor 7 connects electrode 5 to electronic circuits 4. A battery or other electric power source 8 is also arranged in case 2 and is connected to the positive terminal of electronic circuits 4 by a conductor 9.

Electrode 5 forms one of the plates of a capacitive sensor 20 (schematised in FIG. 2), the other plate 21 of this capacitive sensor being formed by the water covering glass 3 when device 1 is immersed. The water allows an electric connection to be established between case 2 of device 1 and glass 3 (symbolised by dots in FIG. 1), which has the effect of returning the potential of the outer face of glass 3 to ground 11 of electronic circuits 4 provided case 2 is connected to the negative terminal of electronic circuits 4 and battery 8.

Device 1 further includes a conventional type of pressure sensor 12, housed in its case 2 and connected to electronic circuits 4 by a conductor 13.

Figure 2:
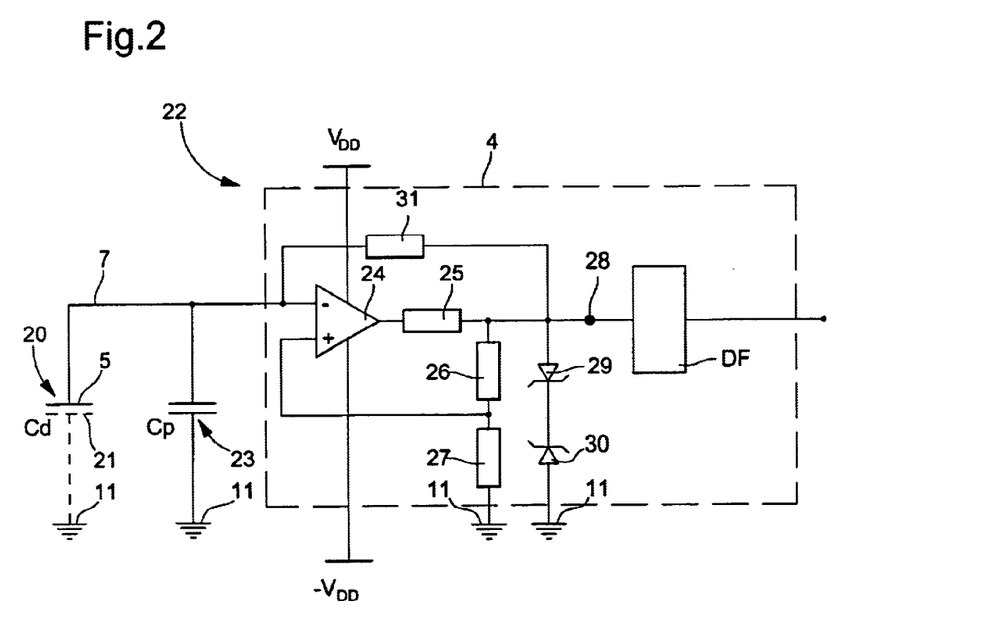
FIG. 2 is a simplified electronic diagram of an embodiment of the means for detecting the presence of water.

FIG. 2 shows a non-limiting example of a preferred embodiment of an electronic circuit for detecting the presence of water 22, used in device 1 of FIG. 1 and which generates an electric control signal in response to activation of capacitive sensor 20. This detection circuit 22 is connected to a frequency detector DF that is in turn connected to a data processing unit (schematised in FIG. 3), which manages the operation of pressure sensor 12 as will be described hereinafter.

Detection circuit 22 includes a capacitive sensor 20 whereas a stray capacitance Cp is present by construction between electrode 5 and case 2 of device 1. This stray capacitance is represented by a capacitor 23 in FIG. 2. Capacitive sensor 20 and capacitor 23 are connected in parallel between ground 11 and the inverting input of an operational amplifier 24.

Detection circuit 22 also includes resistors 25, 26 and 27 all series-connected between the output of amplifier 24 and ground 11. The non-inverting input of amplifier 24 is connected to a junction between resistors 26 and 27. In this configuration, amplifier 24 and resistors 25, 26 and 27 form a Schmidt trigger which supplies at its output 28, i.e. the junction between resistors 25 and 26, a signal having, as a function of the relative values of voltages present at the inverting and non-inverting inputs of amplifier 24, either a high logic level or a low logic level. Two Zener diodes 29 and 30 mounted head-to-toe are connected between output 28 and ground 11, in order to stabilise the voltages respectively defining these logic levels.

Detection circuit 22 also includes a resistor 31 connected between output 28 and the inverting input of amplifier 24. This resistor 31, with capacitive sensor 20 and capacitor 23, forms part of a low-pass filter, which integrates the voltage at the output of the Schmidt trigger. The plate potential of capacitors 20 and 23 is applied to the inverting input of amplifier 24. As a result, detection circuit 22 operates like a voltage-frequency converter, in other words as a voltage controlled oscillator.

In the embodiment illustrated in FIG. 2, the voltage-frequency converter has been designed in the form of an astable multivibrator, since it creates a periodic signal having two quasi-stable states, while oscillating freely. However, it can also be designed in the form of any periodic signal generator and in particular, as was indicated previously, in the form of a voltage controlled oscillator. The arrangement illustrated in FIG. 2 is particularly advantageous because of the simplicity of its manufacture and because no high precision electronic components are required.

The oscillation period T of detection circuit 22 is given by the relationship $$T = 2 \cdot R_{31} \cdot C_{tot} \cdot \ln(1 + (2 \cdot R_{26})/R_{27})$$

where $R_{31}$, $R_{26}$, and $R_{27}$ are respectively the values of resistors 31, 26 and 27, and $C_{tot}$ is the total capacitance between the inverting input of amplifier 24 and ground 11. It can thus be seen that the oscillation frequency of the output signal of the detection circuit is proportional to the inverse of the total capacitance $C_{tot}$ and that therefore the capacitance of the capacitive sensor in conjunction with the stray capacitance determine the value of the oscillation frequency of detection circuit 22.

Thus, the oscillation frequency of the voltage-frequency converter varies as a function of the presence or absence of water on the outer face of glass 3. When device 1 is not immersed in water, plate 21 of capacitive sensor 20 is consequently absent from the circuit shown in FIG. 2. The total capacitance in this case is equivalent to the stray capacitance Cp between electrode 5 and ground 11. The oscillation frequency of the output signal of detection circuit 22 is then proportional to the inverse of stray capacitance Cp.

However, when device 1 is immersed in water, plate 21 is formed and consequently, the capacitive sensor has a capacitance Cd and actually acts on detection circuit 22. In these conditions, the total capacitance $C_{tot}$ is equivalent to the sum of capacitances Cd and Cp.

Thus, in a known manner, the desired data in the output signal of detection circuit 22 is contained in its frequency and one needs only then use simply designed digital means to recover it. By way of example, a pulse counter that is switched on during a fixed operating period, could be implemented. The number of pulses received during this fixed period, directly represents the frequency, and thus the presence or absence of water in contact with glass 3. Those skilled in the art will have no particular difficulty in implementing these means or equivalent means, since they are known in the state of the art.

Figure 3:
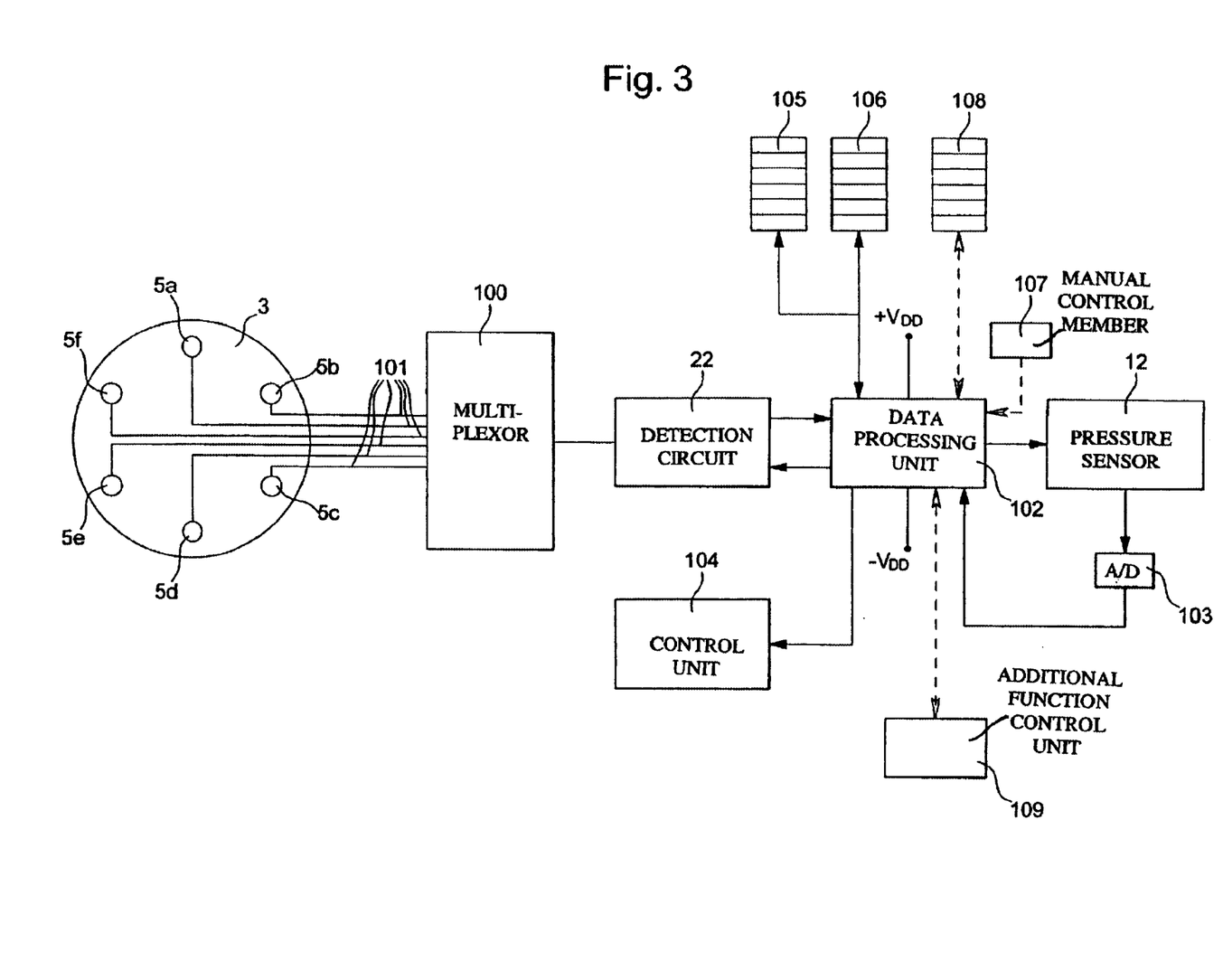
FIG. 3 is a block diagram illustrating an example embodiment of the device according to the present invention in the case where the means for detecting the presence of water include a plurality of capacitive sensors.

FIG. 3 shows, in the form of a block diagram, a preferred embodiment for the set of electronic circuits of device 1 according to the present invention. Only those elements having a direct bearing on the invention have been shown in this Figure.

Glass 3 of device 1 has been schematised in FIG. 3, in a configuration in which capacitive sensors 6 have been provided on its inner face, electrodes 5a to 5f being illustrated. Of course, the following description, relating to this particular embodiment, will also enable those skilled in the art to implement a simplified solution wherein a single sensor is used, the general operating principle remaining the same.

Each of the 6 electrodes 5a to 5f is connected to a conventional type of multiplexer circuit 100, via a conductive path 101, the output of multiplexer circuit 100 being connected to the input of a detection circuit 22 of the type described in relation to FIG. 2. The output of detection circuit 22 is connected to a data processing unit 102, as mentioned previously, the latter also being able to send instructions for controlling detection circuit 22.

Data processing unit 102 is powered by battery 8 of device 1. Processing unit 102 is connected to pressure sensor 12 which, in turn, is capable of producing analogue type electric signals to be sent to an analogue-digital converter 103, itself connected to processing unit 102 for transmitting digital data thereto. Processing unit 102 also includes electric connections to a control circuit 104 for display means (not shown) and two memory zones 105 and 106. It can be seen in FIG. 3 that each of memory zones 105 and 106 has been schematised so as to show six distinct addresses, whose respective functions will be explained hereinafter.

The electronic circuits of device 1 also have a time base (not shown), provided for example by a quartz resonator, delivering a clock signal to processing unit 102 and which can be either directly integrated therein, or arranged at another location in the electronic circuits of device 1, outside the processing unit.

On the basis of the structure that has just been described, the following preferred method is provided for implementing the means for detecting the presence of water in accordance with the present invention.

Device 1 includes at least two operating modes, a specific powering mode and a specific display mode preferably corresponding to each operating mode. A first operating mode, which can be termed the surface mode, is active when device 1 is not immersed in water, whereas a second operating mode, which can be termed the dive mode, is activated when the presence of water has been detected in contact with device 1.

In the surface operating mode, means for measuring the current time and the display thereof by conventional means, can be provided, by way of example. Moreover, as mentioned previously, pressure sensor 12 is preferably powered in this operating mode to carry out periodic measurements of the surrounding pressure, with a predefined period, of a value that can range from 30 minutes to 1 hour approximately. The pressure measurements are stored in a dedicated memory (not shown) to possibly be used subsequently, during a diving exercise. Indeed, if device 1 according to the invention is made in the form of a diving computer, particularly for calculating decompression parameters, during a diving ascent, a decompression algorithm is stored in a specific memory of the electronic circuits. This memory may be directly arranged in processing unit 102. The fact of taking into account a history of the values of the surrounding pressure experienced by the person wearing the watch before the dive, in the decompression algorithm calculations, allows the accuracy of the calculated decompression parameters to be improved.

Of course, those skilled in the art could choose the value of the powering period of pressure sensor 12 in the surface mode, depending on the features of the battery 8 used, the accuracy desired for the decompression parameters and the desired operating autonomy.

Moreover, again on the basis of the clock signal, data processing unit 102 periodically activates the means for detecting the presence of water 20, 22, 100, to determine whether device 1 is immersed in water or not. For this purpose, detection circuit 22 successively measures the capacitance of each of the capacitive sensors associated with electrodes 5a to 5f, via multiplexer 100, to form a first series of measurements S1. The measured quantities are converted into frequencies, preferably in the manner explained hereinbefore in relation to FIG. 2, and then stored in a first 105 of memory zones 105, 106. Thus, each address of memory zone 105 receives a value relating to a given capacitive sensor 20.

At the next powering period of the detection means, typically after 2 to 30 seconds, preferably after around 10 seconds, detection circuit 22 carries out a second series of measurements S2 of the capacitance of each of capacitive sensors 20, via multiplexer 100. This second series of measurements S2 is stored in second memory zone 106, each address of the second memory zone receiving a value relating to a given capacitive sensor.

After storing the second series of measurements S2, data processing unit 102 reads the content of memories 105 and 106 sequentially. At each read step, the processing unit reads the content of the addresses respectively associated with the same capacitive sensor 20 in each of memory zones 105 and 106, in order to calculate the variation that the frequency associated with said given capacitive sensor 20 may have undergone between the two series of measurements S1 and S2. It is then provided that processing unit 102 calculates the variation rate associated with this frequency, to obtain a quantity capable of being subsequently compared to other values, in particular to a reference value predefined by the designer of the device and which is typically around 10%. These operations are carried out successively for all the memory addresses, so as to calculate the frequency variation rate associated with each of the six capacitive sensors. Each of the values obtained for the respective variation rates is compared to the reference value, the latter defining a trigger threshold.

The next series of frequency measurements carried out, at the next powering period, is stored in first memory zone 105, replacing the first series of measurements, to allow comparison thereof with the second series, and so on.

Storage of each new series of measurements is thus always carried out such that the new series replaces the older series previously stored in the corresponding memory zone. Consequently, the comparison is always made between a new series of measurements and the preceding series of measurements, these two series being separated in time by one detection means powering period.

A criterion is provided, to validate or not the presence of water on the basis of the measurements carried out, as a function of the number or proportion of capacitive sensors 20 whose associated frequency variation has exceeded the reference value between two consecutive series of measurements.

By way of example, one could provide that the validation of the presence of water in contact with device 1 is performed when the set of frequencies respectively associated with capacitive sensors 20 has breached the trigger threshold.

One could, however, provide, according to a preferred variant, that the presence of water is validated when a part, for example at least half, of the measured frequencies have varied so as to breach the trigger threshold, instead of all of them.

In fact, when the device is immersed in water, all the quantities respectively associated wit the capacitive sensors normally undergo a variation exceeding the predefined trigger threshold, unless for example the user inadvertently touches one of the capacitive sensors during the series of measurements carried out immediately before immersions. In such case, the series of measurements preceding immersion is stored with a capacitive sensor having a capacitance value corresponding to an activated state, whereas the next series of measurements, carried out while the device is immersed in water, is stored with all the capacitive sensors having an activated state. Thus, the variation rates respectively associated with the capacitive sensors and calculated on the basis of these series of measurements have higher values than the trigger threshold value, predefined for all the capacitive sensors except the one that was activated prior to immersion.

In such case, the measured quantity does not breach the detection threshold for one of the capacitive sensors and the presence of water is not validated if the retained validation criterion for the presence of water corresponds to the simultaneous activation of all the capacitive sensors. The fact of defining a more flexible validation criterion, like for example validating the presence of water when at least half of the capacitive sensors are activated, makes detection of the presence of water more reliable.

Moreover, as was mentioned hereinbefore, the capacitance of a given capacitive sensor is capable of slowly fluctuating over time, because of variations in the surrounding conditions, and the calculation method by comparing successive measurements, used in the present invention, allows calculation errors arising from these fluctuations, to be avoided.

When the trigger threshold is simultaneously breached, i.e. during the same series of measurements, by all of capacitive sensors 20 or by a part of them depending upon the validation criterion used, data processing unit 102 modifies the powering mode of pressure sensor 12. The dive powering mode is activated, during which the frequency of the surrounding pressure measurements carried out by pressure sensor 12 is much higher than in the surface powering mode. One could, for example, provide that the surrounding pressure measurement frequency is of the order of one measurement per second, or even more than one measurement per second.

The surrounding pressure measurements are transmitted to data processing unit 102 via analogue-digital converter 103 to be exploited, either directly by processing unit 102, or by an additional integrated circuit (not shown) connected to the processing unit, on the basis of the decompression algorithm. These calculations enable decompression parameters to be defined, in a known manner and by way of non-limiting example, for the benefit of the person wearing the device during a dive. Signals are then produced by processing unit 102, or by the additional integrated circuit, to be sent to display means control circuits 104, to display particularly the depth of the dive in progress and various decompression parameters. These decompression parameters can for example include the time remaining for the dive in progress before the person wearing the device is obliged to carry out decompression stages during the ascent, or data relating to any decompression stages to be observed during the ascent.

Those skilled in the art will have no particular difficulty in finding a compromise between improved accuracy in the calculations carried out by the decompression algorithm, because of a high pressure measurement frequency, and limited power consumption by the pressure sensor, to maintain reasonable autonomy for device 1.

Of course a very simple device 1 could be implemented, that could mainly or exclusively indicate the (quasi) instantaneous depth to its user, from the moment when immersion has been detected by the means for detecting the presence of water according to the invention.

Preferably, the means for detecting the presence of water are also powered when device 1 is in the dive powering mode, with the same powering frequency as in the surface mode. As long as device 1 remains immersed, the respective values of the capacitances of the various capacitive sensors do not vary much between two successive series of measurements.

However, each of these values undergoes a new significant variation when device 1 is removed from the water, which is detected by data processing unit 102, via the circuit for detecting the presence of water 22 and the measurements successively stored in memory zones 105 and 106. Detection of a variation breaching the trigger threshold, this new variation occurring in the opposite direction from that occurring at the moment of entry into the water, simultaneously for all of capacitive sensors 20, or part of them depending on the validation criterion used, causes data processing unit 102 to deactivate the dive powering mode to activate the surface powering mode.

Since the method for detecting the absence of water is based on the same principle as that described hereinbefore in relation to the detection of the presence of water, it will not be described in more detail.

It should be noted that the description that has just been given in relation to FIG. 3 is also valid if the means for detecting the presence of water include only one capacitive sensor 20. Electronic circuits 4 of device 1 can be made identically or can be simplified to keep only the necessary elements. In such case, multiplexer 100 can be omitted and memories 105 and 106 can be simplified to each include only one memory address. The operation of electronic circuits 4 thus simplified remains similar to that which has been described, i.e. based on a principle of successive compared measurements.

In an alternative embodiment with a single capacitive sensor, the corresponding electrode can have a surface area substantially equal to the area of the inner surface of the glass. In such case, the validation criterion for detecting the presence of water can be adjusted as a function of a certain proportion of the surface area of the covered glass. Thus, a capacitance value variation threshold can be predefined, corresponding for example to 50% cover of the glass surface area, from which the data processing unit deems that the electronic device is in contact with water.

Moreover, it should be noted that the number of memory zones and their operating mode described hereinbefore are not limiting. Indeed, one could provide a number of memory zones greater than two to allow comparison of the last series of measurements with several preceding series of measurements rather than simply with the last. Thus, three of four memory zones could be provided in which the series of measurements are stored alternately, without departing from the scope of the embodiment that has just been described.

Likewise, a variant can be provided wherein four memory zones, for example, operating like a shift register, i.e. storage of a new series of measurements still occurs in the first memory zone whereas the content of a memory zone or row i is stored in memory zone i+1. This is how the content of the last memory zone, the fourth in the present example, which corresponds to the oldest series of measurements is deleted to be replaced by the content of the third memory zone, the latter being replaced by the content of the second memory zone which is itself replaced by the content of the first memory zone. In this way, the processing unit can be programmed to compare simultaneously the new series of measurements with the three preceding series of measurements, which increases the reliability of detection of the presence of water.

Those skilled in the art will not encounter any particular difficulty in implementing the number of memory zones best suited to their particular case and operation, in order to find the best compromise between the space occupied by the memory zones in the electronic circuits and the reliability of detection of the presence of water.

An advantageous alternative for the embodiment in which the means for detecting the presence of water include a plurality of capacitive sensors 20 consists in attributing an additional manual control member function to capacitive sensors 20.

In such case, the following structure and operation are provided, in an advantageous and non-limiting manner.

The device includes a conventional type of manual control member 107, such as a push-button, capable of activating a specific command in processing unit 102, when it is activated. The device further includes an additional memory zone 108 including at least one memory address per capacitive sensor 20, thus shown in FIG. 3 with six memory addresses.

The invention also provides that one operating mode, or one function, is associated with each of the capacitive sensors and is activated in response to an action exerted on the corresponding capacitive sensor, by placing the user's finger opposite one of electrodes 5a to 5f. For this purpose, the electronic circuits can include a unit 109 for controlling the additional functions respectively associated with the capacitive sensors.

In a known manner, the capacitive sensor control member function is not permanently active, for obvious reasons of electric power consumption and to prevent the functions respectively associated with the capacitive sensors from being inadvertently activated.

Thus, data processing unit 102 is made such that the manual control member function for capacitive sensors 20 is activated in response to an action by the user detected on control member 107.

For this purpose and in order to allow reliable detection of a user's finger placed on one of the capacitive sensors, in response to an action detected on control member 107, data processing unit 102 activates detection means 20, 22, 100, to measure successively the capacitance of each of the capacitive sensors associated with electrodes 5a to 5f, via multiplexer 100. The first series of measurements thus obtained is then stored in memory zone 108 to form a reference series, which removes the aforementioned problems of fluctuation over time of the capacitance values of sensors 20.

New series of measurements are then carried out successively during a predefined period, preferably of the order of 20 seconds, during which the detection means are continuously powered. At the same time, each measured quantity associated with a given capacitive sensor 20, as explained hereinbefore, is compared to the corresponding reference value in memory zone 108.

As previously described, the comparison method employed is preferably based on a calculation of the rate of variation between the reference measurement and each new measurement. When the rate of variation calculated for one of capacitive sensors 20 exceeds the previously described predefined threshold value during the measurements, the excess is interpreted by data processing unit 102 as meaning a command to activate the function associated with the capacitive sensor concerned. The associated function is then activated either directly by processing unit 102, or via an additional function control unit 109, if appropriate. Moreover, the adapted electric signals are sent to display means control circuits 104 for displaying the data relating to the new function activated. The functions capable of being implemented in the present device are of any known conventional type, such as chronograph, alarm, time zone change or even thermometer, compass or altimeter functions, this list being in no way exhaustive or limiting.

As mentioned hereinbefore, after a predefined period of the order of 20 seconds, if none of the measured quantities has breached the trigger threshold at least once during successive series of measurements, processing unit 102 interrupts the continuous power supply to detection means 20, 22, 100.

On the basis of the particular operation that has just been described, it is preferably provided that detection means 20, 22, 100 simultaneously ensure their function of detecting the presence of water in contact with the device according to the invention.

Thus, data processing unit 102 continues to calculate, on the basis of the clock signal, time intervals corresponding to the period defined hereinbefore in relation to the periodic powering of detection means 20, 22, 100. Moreover, processing unit 102 commands storage of the series of measurements occurring substantially at the end of each interval in memory zones 105 and 106 alternately, if necessary, i.e. particularly in the case of a detection means powering period fixed at less than 20 seconds. Likewise, two consecutive series of measurements are used to calculate the rate of variation in the measured quantity for each capacitive sensor and the dive powering mode is activated in response to a breach of the predefined variation threshold for all the capacitive sensors or a part of them, simultaneously, as previously described.

Preferably, the operation of capacitive sensors 20 as manual control members is interrupted as soon as the presence of water has been detected in contact with the device. Moreover, if a specific additional function control unit 109 is provided, it is also deactivated when the presence of water has been detected.

It should be noted that alternatives are possible as far as the choice of the criterion validating the presence of water is concerned, these alternatives being, of course, included within the teaching of the present invention. By way of example, if the detection means include a plurality of capacitive sensors, one can provide an additional step for processing the frequency measurements carried out, prior to carrying out the variation rate calculation. This additional processing step can be achieved in the form of a calculation of the mean value of measurements obtained during a series for all of the capacitive sensors, two mean values respectively calculated for two consecutive series of measurements being then compared with each other, via a corresponding variation rate calculation, as previously described.

Thus, the criterion for validating the presence of water can be defined with respect to the variation rate calculation calculated for the mean frequency respectively associated with capacitive sensors 20. In such case, it is clear that the more capacitive sensors the device includes, the more reliable the detection of the presence of water will be.

Alternatively, the first embodiment described hereinbefore could be completed, based on the frequency variation rate calculation for each of the capacitive sensors, by adding a filter function to data processing unit 102. Indeed, one could provide that, if in a given series of measurements, only one of capacitive sensors 20 is activated because of accidental contact or the use of its control member function, the processing unit replaces the new value of its associated frequency with the frequency value stored during the preceding series of measurements, in the storage step in one of memory zones 105, 106.

In such case, the aforementioned criterion for validating the presence of water based on simultaneous activation of all the capacitive sensors is applicable, without raising the problem of reliability as regards the detection of the presence of water.

Of course, those skilled in the art will not encounter any particular difficulty in implementing other comparison means equivalent to those that have just been described, without departing from the scope of the present invention.

Moreover, the preceding description attempts to describe particular embodiments by way of non limiting illustration and the invention is not limited, for example, to the number or positioning described for the capacitive sensors. In particular, one could arrange a capacitive sensor at the centre of the glass of the device, or even arrange at least one or all of the capacitive sensors in suitable different areas of the assembly formed by the case and the glass of the device according to the present invention.

We claim:

1. A portable electronic device including powering means for powering electronic circuits including a data processing unit, said electronic circuits being housed in an assembly formed by a case closed by a glass, the device further including a pressure sensor and means for detecting the presence of water capable of producing electric signals to be sent to said data processing unit, said detection means including at least one capacitive sensor including a capacitor, one plate of which is formed by an electrode arranged on an inner region of the case-glass assembly and whose capacitance is capable of varying following a modification in nature of the external medium located directly in contact with an external region of the case-glass assembly opposite the electrode, said region coming into contact with water, wherein said pressure sensor operates in at least two powering modes, a first mode is the surface mode and a second is the dive mode and wherein said detection means are periodically activated to carry out measurements of a quantity representative of the value of the capacitance of said capacitor, said electronic circuits further including means for comparing at least two successive measurements of said quantity and producing an electric signal for activating said dive powering mode in response to a variation in said capacitance between two successive measurements of said quantity higher than a predefined value.

2. The device according to claim 1, wherein said electrode is transparent and arranged on the inner face of said-glass, wherein said electrode has a surface area substantially equal to the surface area of said inner face of the glass and wherein said predefined value corresponds to the variation that said measured quantity undergoes between a first external medium and a second external medium when said second external medium enters into contact with said glass over a surface area representing a predefined portion of the surface area of said electrode.

3. The device according to claim 1, the device including at least one control member, preferably of the push-button type, said electrodes being transparent and arranged on the inner face of said glass, at least one of said capacitive sensors being also capable of assuring an additional control member function in said surface mode in response to an action on said control member.

4. The device according to claim 1, said detection means including, in particular, additional means for converting a first electric signal whose amplitude depends on the capacitance value of said capacitor(s) into a second periodic electric signal whose frequency depends on said capacitance and corresponds to said measured quantity.

5. The device according to claim 1, wherein said pressure sensor carries out periodic measurements of the surrounding pressure, preferably every hour, in said surface powering mode, whereas it measures the surrounding pressure almost in real time in said dive mode.

6. A portable electronic device including powering means for powering electronic circuits including, in particular, a data processing unit, said electronic circuits being housed in an assembly formed by a case closed by a glass, the device further including a pressure sensor and means for detecting the presence of water capable of producing electric signals to be sent to said data processing unit, wherein said pressure sensor is capable of operating in at least two powering modes, a first mode is the surface mode and a second is the dive mode and wherein means for detecting the presence of water include at least a first and a second capacitive sensor each including a capacitor, one plate of which is formed by an electrode arranged on an inner region of the case-glass assembly and whose capacitance is capable of varying following a modification in nature of the external medium located directly in contact with an external region of the case-glass assembly opposite the electrode, said region coming into contact with water, said detection means being periodically activated to carry out measurements of a first, respectively a second quantity representative of the value of the capacitance of said first, respectively said second capacitor, said electronic circuits further including means for comparing at least two successive measurements of said first quantity, respectively said second quantity and producing an electric signal for activating said dive powering mode if the variations respectively in said first and second quantities, between two successive measurements, are simultaneously higher than a predefined value.

7. The device according to claim 6, wherein said detection means include at least three capacitive sensors, wherein said capacitive sensors are arranged substantially regularly in proximity to the periphery of said glass and wherein said detection means produce said activating dive powering mode signal if at least half of said quantities associated respectively with said capacitive sensors simultaneously undergo respective variations, between two successive measurements, higher than said predefined value.

8. The device according to claim 7, said electronic circuits including multiplexing means for carrying out, at each activation period of said detection means, one measurement per capacitive sensor to form a series of measurements of said quantities respectively associated with said respective capacitive sensors, two successive series of measurements being stored alternately in a first and a second memory zone so as to calculate, after each series of measurements, the respective variations in each of said quantities between the last series of measurements and the preceding series of measurements.

9. The device according to claim 7, said electronic circuits including multiplexing means for carrying out, at each activation period of said detection means, one measurement per capacitive sensor to form a series of measurements of said quantities respectively associated with the respective capacitive sensors, said data processing unit being capable of calculating the mean values of said series of measurements respectively associated with said capacitive sensors, said mean values being stored respectively and alternately in a first and a second memory zone so as to calculate after each series of measurements the respective variations in each of said mean values between the last series of measurements and the preceding series of measurements, said predefined value being defined relative to the mean value of a series of measurements.

10. The device according to claim 6, said electronic circuits including multiplexing means for carrying out, at each activation period of said detection means, one measurement per capacitive sensor to form a series of measurements of said quantities respectively associated with said respective capacitive sensors, two successive series of measurements being stored alternately in a first and a second memory zone so as to calculate, after each series of measurements, the respective variations in each of said quantities between the last series of measurements and the preceding series of measurements.

11. The device according to claim 6, said electronic circuits including multiplexing means for carrying out, at each activation period of said detection means, one measurement per capacitive sensor to form a series of measurements of said quantities respectively associated with the respective capacitive sensors, said data processing unit being capable of calculating the mean values of said series of measurements respectively associated with said capacitive sensors, said mean values being stored respectively and alternately in a first and a second memory zone so as to calculate after each series of measurements the respective variations in each of said mean values between the last series of measurements and the preceding series of measurements, said predefined value being defined relative to the mean value of a series of measurements.

12. The device according to claim 6, the device including at least one control member, preferably of the push-button type, said electrodes being transparent and arranged on the inner face of said glass, at least one of said capacitive sensors being also capable of assuring an additional control member function in said surface mode in response to an action on said control member.

13. The device according to claim 6, said detection means including, in particular, additional means for converting a first electric signal whose amplitude depends on the capacitance value of said capacitor(s) into a second periodic electric signal whose frequency depends on said capacitance and corresponds to said measured quantity.

14. The device according to claim 6, wherein said pressure sensor carries out periodic measurements of the surrounding pressure, preferably every hour, in said surface powering mode, whereas it measures the surrounding pressure almost in real time in said dive mode.

15. A method for detecting the presence of water in contact with a portable electronic device including powering means for powering electronic circuits including, in particular, a data processing unit, said electronic circuits being housed in an assembly formed by a case closed by a glass, a pressure sensor operating in at least two powering modes, a first mode is the surface mode and a second is the dive mode, the device further including detection means capable of producing electric signals to be sent to said data processing unit, said means for detecting the presence of water including at least one capacitive sensor including a capacitor, one plate of which is formed by an electrode arranged on an inner region of the case-glass assembly and whose capacitance is capable of varying following a modification in the nature of the external medium located directly in contact with an external region of the case-glass assembly opposite the electrode, such as said region coming into contact with water, said detection means being periodically activated to carry out measurements of a quantity representative of the value of the capacitance of said capacitor, the method including the periodic steps of:

a) measuring the value of said quantity;

b) calculating, at each new measurement of said quantity, the variation between its new value and the preceding value;

c) activating the dive powering mode if said variation has a higher value than a predefined value or, if not, starting at step (a) again during the next period.

16. The method according to claim 15, wherein said electronic circuits include at least two memory zones for storing, at each powering period of said detection means, the value measured for the quantity representative of the value of the capacitance of said capacitor, said memory zones being used alternately from one period to the next in order to allow, after each new measurement of said quantity, the calculation to be carried out of the variation in said new value with respect to the preceding one.

17. The method according to claim 16, the detection means including n capacitive sensors n being at least equal to two, each of said memory zones including at least n memory addresses, wherein the method includes the steps of:

a) measuring, during a powering period of said detection means, the value of said quantity for each of said n capacitive sensors so as to form a series of n measurements;

b) calculating, at each new series of measurements, each variation between the new value of the quantity relating to each of said capacitive sensors and the corresponding preceding value;

c) activating the dive powering mode if at least half of said n variations calculated at step (b) simultaneously have respective values higher than a predefined value or, if not, starting at step (a) again during the next period.

18. The method according to claim 17, said detection means including multiplexing means and means for converting a first electric signal whose amplitude level is representative of the value of the capacitance of a capacitor into a second electric signal whose frequency is representative of said capacitance value, said measured quantity corresponding to a frequency, a series of n measurements being carried out by using said multiplexing means.

19. The method according to claim 16, the detection means including n capacitive sensors, n being at least equal to two, wherein the method includes the steps of:

a) measuring, during a powering period of said detection means, the value of said quantity for each of said n capacitive sensors so as to form a series of n measurements;

b) calculating, at each new series of measurements, the mean value of said n measurements obtained;

c) calculating each variation between the new value of the mean calculated in step (b) and the mean value corresponding to the preceding series of measurements;

d) activating the dive powering mode if the variation calculated at step (c) has a higher value than a predefined value or, if not, starting at step (a) again during the next period.

20. The method according to claim 15, wherein the powering period of the detection means has a value comprised between around 2 and 30 seconds, preferably of the order of 10 seconds.

* * * * *